United States Patent [19]

Gristina et al.

[11] Patent Number: 5,718,899
[45] Date of Patent: *Feb. 17, 1998

[54] METHOD AND COMPOSITIONS FOR DIRECT CONCENTRATED DELIVERY OF PASSIVE IMMUNITY

[76] Inventors: Anthony George Gristina, 11605 Deer Forest Rd., Reston, Va. 22094; Quentin Newell Myrvik, 404 Palmetto Dr., Caswell Beach, N.C. 28465

[*] Notice: The term of this patent shall not extend beyond the expiration date of Pat. No. 5,505,945.

[21] Appl. No.: 608,817

[22] Filed: Feb. 29, 1996

Related U.S. Application Data

[62] Division of Ser. No. 295,482, Aug. 25, 1994, Pat. No. 5,505,945, which is a continuation of Ser. No. 3,305, Jan. 12, 1993, abandoned.

[51] Int. Cl.$^6$ .................... A16K 39/40; A16K 39/085; A16K 39/09; A16K 39/104
[52] U.S. Cl. .................... 424/164.1; 424/150.1; 424/130.1; 424/163.1; 424/165.1; 424/169.1; 424/170.1; 530/387.1; 530/388.1; 530/388.2; 530/388.4; 530/389.1; 530/389.5
[58] Field of Search .................... 424/164.1, 150.1, 424/130.1, 163.1, 165.1, 169.1, 170.1; 530/387.1, 388.1, 388.2, 388.4, 389.1, 389.5

[56] References Cited

U.S. PATENT DOCUMENTS

| | | |
|---|---|---|
| 4,412,990 | 11/1983 | Lundblad et al. |
| 4,714,612 | 12/1987 | Nakamura et al. |
| 4,770,875 | 9/1988 | Kume et al. |
| 4,784,989 | 11/1988 | Hook et al. |
| 4,859,769 | 8/1989 | Karlsson et al. |
| 4,957,735 | 9/1990 | Huang |
| 4,957,739 | 9/1990 | Berget et al. |
| 4,980,462 | 12/1990 | Karlsson et al. |
| 4,994,269 | 2/1991 | Collins et al. |

FOREIGN PATENT DOCUMENTS

| | | |
|---|---|---|
| 0127712 | 6/1983 | European Pat. Off. |
| 0168830 | 7/1985 | European Pat. Off. |
| 0201004 | 4/1986 | European Pat. Off. |
| 2186592 | 8/1987 | United Kingdom |

OTHER PUBLICATIONS

Gristina, "Biomaterial-Centered Infection: Microbial Adhesion Versus Tissue Integration", Science, vol. 237, 25 Sep. 1987, pp. 1588–1595.
Gristina et al., "Biomaterial-Centered Sepsis and the Total Artificial Heart", Journal of the American Medical Association (JAMA), vol. 259, Feb. 12, 1988, pp. 870–874.
Gristina et al., "Molecular Mechanisms in Musculoskeletal Sepsis: The Race for the Surface", Instructional Course Lectures, vol. XXXIX 1990, American Academy of Orthopaedic Surgeons, pp. 471–482.
Buckley et al., "The Use of Intravenous Immune Globulin in Immunodeficiency Diseases" New England Journal of Medicine, Jul. 11, 1991, pp. 110–117.
Cometta et al., "Prophylactic Intravenous Administration of Standard Immune Globulin . . . ", New England Journal of Medicine, vol. 327, No. 4, Jul. 23, 1992, pp. 234–239.
Siber et al., "Use of Immune Globulins in the Prevention and Treatment of Infections" Current Clinical Topics in Infectious Diseases, vol. 12 pp. 208–256.
Panillio et al., "Methicillin–Resistant Staphylococcus Aureus in U.S. Hospitals, 1975–1991", Infection Control and Hospital Epidemiology, vol. 13, No. 10, Oct. 1992, pp. 582–586.
Emori et al., "Nosocomial Infections in Elderly Patients in the United States, 1986–1990", American Journal of Medicine, vol. 91(suppl 3B), pp. 3B–289S–293S.
Siber, "Immune Globulin to Prevent Nosocomial Infections", New England Journal of Medicine, vol. 327, No. 4, pp. 269–271.
Ma, "Prevention of Colonization of Streptococcus Mutans by Topical Application of Monoclonal Antibodies . . . ", Arch Oral Biol 1990; 35 Suppl;115S–122S(abstract).
Gristina, "Materials, Micobes and Man: the Problem of Infection Associated With Implantable Devices", Current Perspective on Implantable Devices, vol. 1, JAI Press Inc., pp. 71–137.
Gristina, "Biomaterial Specificity, Molecular Mechanisms and Clinical Relevance of S. epidermidis and S. aureus Infections in Surgery", Zbl. Bakt. Suppl. 16, Gustav Fischer Verlag, 1987.
Kojima, "Antibody to the Capsular Polysaccharide/Adhesion Protects Rabbits . . .", Journal of Infectious Diseases 1990;162, Aug., pp. 435–441.
Mandell (ed.), *Principles and Practice of Infectious Diseases*, 2nd Ed., John Wiley and Sons, 1985, Chapter 5, pp. 37–43.

(List continued on next page.)

*Primary Examiner*—Susan A. Loring
*Attorney, Agent, or Firm*—Whitham, Curtis, Whitham & McGinn

[57] ABSTRACT

Compositions containing a high concentration of the full repertoire of immunoglobulins, including IgA, IgM and IgG, are used to combat infections from microorganisms and viruses at a wound, surgical, or burn site, or normal tissue at times of risk of infection. The compositions can contain elevated antibody titers for several specific pathogens including *S. aureus*, CNS, Enterococci, *S. epidermidis*, *P. aeruginosa*, *E. coli*, and *Enterobacter spp.*, etc. The compositions are applied directly to a wound or burn site as an ointment, creme, fluid, spray, or the like, prior to vital or bacterial attachment or biofilm formation such that adhesion of the pathogens is inhibited and the pathogens closest to the wound or burn site will be pre-opsonized for phagocytic killing prior to toxin release. The immunoglobulins in the composition can be immobilized on a biocompatible material such as collagen, fibrin, hyaluronan, biodegradable polymers, and fragments thereof, which will be placed in-situ at the wound, surgical or burn site. In addition, the immunoglobulins in the composition may be coated on the body contacting surface of an implantable device such as a catheter, contact lens or total joint. The inventive compositions have particular application in preventing infections.

12 Claims, No Drawings

OTHER PUBLICATIONS

Behre et al., "Endotoxin Concentration in Neutropenic Patients with Suspected Gram-Negative Sepsis", Antimicrobial Agents and Chemotherapy, vol. 36, No. 10, Oct. 1992, pp. 2139–2146.

van Furth et al., "Correlation Between Opsonic Activity for Various Microorganisms and Composition of Gammaglobulin Preparations for Intravenous Use", Journal of Infectious Diseases, vol. 149, No. 4, Apr. 1984, pp. 511–517.

Givner et al., "A Polyclonal Human IgG Preparation Hyperimmune for Type III, Group B Streptococcus", Journal of Infectious Diseases, vol. 158, No. 4, Oct. 1988, pp. 724–728.

Emori et al., "National Nosocomial Infections Surveillance System (NNIS) ... ", American Journal of Infection Control, vol. 19, No. 1, Feb. 1991, pp. 19–35.

Culver et al., "Surgical Wound Infection Rates by Wound Class, Operative Procedure, and Patient Risk Index", American Journal of Medicine, vol. 91(Suppl 3B), Sep. 16, 1991, pp. 38–B 3B–152S–157S.

"Nosocomial Infection Rates for Interhospital Comparison ... ", Infection Control and Hospital Epidemiology, vol. 12, No. 10, pp. 609–621.

Jarvis et al., "Nosocomial Infection Rates in Adult and Pediatric Intensive Care Units in the United States", American Journal of Medicine, vol. 91(Supp3B) Sep. 16, 1991, pp. 185S–191S.

Horan et al., "Pathogens Causing Nosocomial Infections", Antimicrobic Newsletter, vol. 5, No. 9, Sep. 1988, pp. 66–68.

MedImmune, Inc. 1991 Annual Report.

Pirofski et al., "Current State of the Hybridoma Technology", Journal of Clinical Immunology, vol. 10, No. 6 (Nov. Suppl. 1990), pp. SS–14S.

Dwyer, "Manipulating the Immune System With Immune Globulin", New England Journal of Medicine, vol. 326, No. 2, Jan. 9, 1992, pp. 107–116.

Givner, "Human Immunoglobulins for Intravenous Use ... ", Pediatrics, vol. 86, No. 6, Dec. 1990, pp. 955–962.

Steinman, "The Use of Monoclonal Antibodies for Treatment of Autoimmune Disease", Journal of Clinical Immunology, vol. 10, No. 6, (Nov. 1990 Supp) pp. 30S–39S.

Waldmann et al. "Lymphokine Receptor–Directed Therapy: A Model of Immune Intervention", Journal of Clinical Immunology, vol. 10, No. 6 (Nov. 1990 Supp) pp. 19s–29s.

Vitetta, "Immunotoxins: New Therapeutic Reagents for Autoimmunity, Cancer and Aids, Journal of Clinical Immunology", vol. 10, No. 6 (Nov. 1990 Supp), pp. 15S–18S.

"Investment Opinion and Summary", Smith Barney, Aug. 31, 1992.

Gristina et al., "Microbes, Metals, and Other Nonbiological Substrate in Man", Orthopaedic Infection, W.B. Saunders Co., 1989, Chapter 3, pp. 26–36.

Gristina et al., "Microbial Adhesion and the Pathogenesis of Biomaterial–Centered Infections", Orthopaedic Infection, W.B. Saunders Co., 1989, Ch 2, pp. 3–25.

Gistina et al., "Biomaterial–Centered Infections: Microbial Adhesion versus Tissue Integration", Pathogenesis of Wound and Biomaterial–Associated Infections, Springer–Verlag, pp. 193–216.

Anwar et al., "Effective Use of Antibiotics in the Treatment of Biofilm–Associated Infections", ASM News, vol. 58, No. 12, 1992, pp. 665–668.

Casadevall et al., "Serum Therapy Revisited: Animal Models of Infection and Development of Passive Anibody Therapy" Antimicrobial Agents and Chemotherapy, Aug. 1994, pp. 1695–1702.

Collins, M.S. et al, Infection, 15 Suppl. 2:551–559, 1987.

Sherertz et al., "Efficacy of Antibiotic–Coated Catheters in Preventing Subcutaneous Staphylococcus aureus Infection in Rabbits," Journal of Infectious Diseases, 167:98–106, 1993.

Seligson et al., "The Use of Antibiotic–Impregnated Polymethylmethacrylate Beads to Prevent the Evolution of Localized Infection," Journal of Orthopedic Trauma, vol. 6, No. 4, pp. 401–401 (1992).

Collins et al., "Therapy of Experimental Pseudomonas Aeruginosa burn wound sepsis with human immunoglobulin G. Pseudomonas hyperimmune immunoglobulin G, and antibiotics," The Pathophysiology of Combined Injury and Trauma, Eds. Gruber, Walker, MacVittie and Conklin, Academic Press, 1987.

Norden, "Osteomyelitis: Lessons from Animal Models and Clinical Application," Musculoskeletal Infection Eds. Esterhai, Gristina, Poss, American Academy of Orthopaedic Surgeons, Dallas, Texas, 1990.

Norden, "Lessons Learned from Animal Models in Osteomyelitis," Review of Infectious Diseases, Jan.–Feb. 1988, 103–110.

Rissing, "Animal Models of Osteomyelitis," Infectious Diseases Clinics of North America, Ed. Norden, W.B. Saunders Co., Sep. 1990.

Andriole, "A Paradigm of Human Chronic Osteomyelitis," The Journal of Bone and Joint Surgery, vol. 55–A, No. 7, Oct. 1973.

Whalen, "A Histological Study of Acute Hematogenous Osteomyelitis following Physical Injuries in Rabbits," The Journal of Bone and Joint Surgery, pp. 1383–1392 Oct., 1988.

Worlock, "The Prevention of Infection in Open Fractures," The Journal of Bone and Joint Surgery, pp. 1341–1347, Oct. 1988.

Ramisse et al, "Passive Local Immunotherapy of Experimental Staphyloccal Pheumonia with Human Intravenous Immunoglobulin," Journal of Infectious Diseases 168:1030–3, 1993.

Costerton et al., "Behaviour of Bacteria in Biofilms" ASM News vol. 55, No. 12, 1989, pp. 650–654.

Georg Peters "New Considerations in the pathenogenesis of coagulase–negative staphylococcal foreign body infections" Journal of Antimicrobial Chemotherapy (1988) 21, Suppl. C. 139–148.

Tsukayama et al., "Microbiology of Prosthetic–Joint Infections," Complications in Orthopedics Nov./Dec. 1993, pp. 70–74.

Cheml, "Role of Monoclonal Antibody Therapy in the Treatment of Infectious Disease," American Journal of Hospital Pharmacy vol. 47, Nov. 1990 Supp 3 pp. S11–S15.

Hall, "IL–12 Holds Promise Against Cancer, Glimmer of AIDS Hope," Science, vol. 263, Mar. 25, 1994, pp. 1685–1686.

METHOD AND COMPOSITIONS FOR DIRECT CONCENTRATED DELIVERY OF PASSIVE IMMUNITY

CROSS-REFERENCE TO RELATED APPLICATIONS

This application is a divisional patent application of the patent application having U.S. Ser. No. 08/295,482 filed Aug. 25, 1994, now U.S. Pat. No. 5,505,945, which itself was a continuation application of the patent application having U.S. Ser. No. 08/003,305 filed Jan. 12, 1993, now abandoned. In addition, this application is related to the co-pending patent application having Ser. No. 08/441,299 filed May 15, 1995, now U.S. Pat. No. 5,530,102, which itself was a divisional of the patent application having Ser. No. 08/003,305, abandoned. The complete contents of each of these patent applications being herein incorporated by reference.

This invention was made with government support under AR26957 and GM35939, both of which were awarded by the National Institutes of Health. The government has certain rights in the invention.

BACKGROUND OF THE INVENTION

1. Field of the Invention

The invention is directed to the in situ precoating and preopsonization by direct application of a full repertoire of immunoglobulins (IgG, IgA, IgM, and parts thereof) to the surfaces of tissues and biomaterials for the prevention and treatment of microbial adhesion, colonization, and infection in man and animals.

2. Description of the Prior Art

Surgical wound infection, especially biomaterial centered, or sepsis subsequent to major trauma with bacterial contamination, continues to be a significant problem in morbidity and cost even with the use of antibiotics. There are twenty five million surgeries each year in the United States and an equivalent number in Europe. Although rates of infection are quite low for most elective surgeries, they are significantly higher in the presence of biomaterial implants or traumatized tissue and range from less than 1% for total hips, to 6% for vascular grafts, half of which culminate in amputation or death. The rate of infection for the total artificial heart is essentially 100% if awaiting bridge to transplant for more than ninety days. Most often, and interestingly, infections about biomaterials cannot be cured without removal of the implant, even with massive doses of antibiotics. Major contaminated wounds and open fractures such as occur in industry, auto trauma, and warfare also have up to and more than a 10% rate of sepsis. Biomaterial centered infection is discussed in Gristina, *Science*, 237:1588–1595 (1987), Gristina et al., *JAMA*, 259:870–874 (1988), and Gristina et al., "Molecular Mechanisms in Musculoskeletal Sepsis: The Race for the Surface", Chapter 58 of *Instructional Course Lectures*, Vol. XXXIX 1990, ed. Greene, American Academy of Orthopaedic Surgeons.

All burns are colonized by bacteria. Large 2° and 3° burns produce severe local and systemic sepsis, toxin release, additional tissue destruction, and bacteremia.

Streptococcal infections, endocarditis, and pneumonia also persist as serious problems for at risk groups. Tuberculosis and secondary opportunistic pathogens are among the recurring diseases in immuno compromised patients (AIDs). For these diseases, antibiotics are often ineffective, not timely or deliverable. Respiratory, genitourinary, and gynecologic mucosal surfaces are vulnerable to recurrent and chronic bacterial and viral invasion.

The two important causal mechanisms for these infections are: (1) microbial adhesion to damaged tissue or biomaterial substrata and the formation of bacterial biofilms which shield microorganisms from host defenses and antibiotics, and (2) disruption of host defenses and the production of an immunoincompetent inflammatory zone at damaged tissues and biomaterial interfaces. Biomaterial surfaces, their particulate debris, severe tissue trauma, and burns cause massive and chronic inflammatory responses characterized by host defense mechanism exhaustion. Additionally 1° and 2° immuno deficiency states (e.g., AIDs, the aged, diabetics, etc.) cause increased host susceptability to pathogens.

Currently antibiotics are the treatment of choice for most bacterial diseases, but they tend to be ineffective against contaminated open fracture, biomaterial centered, foreign body and burn infections, cannot be extensively used to preempt infection, and do not potentiate host defenses. Antibiotics and host defenses (immunoglobulins) usually are ineffective after bacteria have formed protective biofilms (see, Gristina, *Science*, 237:1588–1595 (1987), Gristina et al., *JAMA*, 259:870–874 (1988), and Gristina et al., "Molecular Mechanisms in Musculoskeletal Sepsis: The Race for the Surface", Chapter 58 of *Instructional Course Lectures*, Vol. XXXIX 1990, ed. Greene, American Academy of Orthopaedic Surgeons). Furthermore, use of antibiotics causes selection for the survival of drug-resistant strains.

Higher animals have, by evolution, established several very effective means of defense against microbes involving the immune system. Invading bacteria are rapidly identified, via complement and immunoglobulin opsonization, phagocytized and destroyed by the cellular immune system and white blood cells (neutraphils and macrophages). Globulins are essentially nature's perfect antibodies. Complement, available as a precursor protein which is activated by the presence of microorganisms and globulins, also functions in antibacterial activities. Opsonization of foreign organisms is the memory component of the immune system. After previous antigenic exposure, the immune system produces a series of globulins which attach to and coat bacteria or neutralize viruses so that they are readily recognized, phagocytosed and destroyed by neutrophils and macrophages. Foreign proteins of invading organisms also stimulate a humoral immune response which over a period of time (3–6 weeks) amplifies the numbers of cells designed to recognize and destroy specific invaders. Tables 1 and 2 present the antimicrobial functions of immunoglobulins and the metabolic properties of immunoglobulins.

TABLE 1

Antimicrobial functions:
(1) Bacterial lysis (requires complement)
(2) Opsonization (enhanced by complement)
(3) Toxin neutralization
(4) Viral neutralization (may be enhanced by complement)
(5) Mediates antibody dependent cell mediated cytoxicity (ADCC)

(6) Synergistic activity with antibiotics

TABLE 2

Metabolic Properties of Immunoglobulins

|  | IgG | IgA | IgM | IgD | IgE |
|---|---|---|---|---|---|
| Serum Level Mean (mg/dl) (range) | 989 (600– 1600) | 200 (60– 330) | 100 (45– 150) | 3 | 0.008 |
| Total Body Pool mean (mg/kg) (range) | 1030 (570– 2050) | 210 | 36 | 1.1 | 0.01 |
| Synthesis rate mean (mg/kg/day) | 36 | 28 | 2.2 | 0.4 | 0.004 |
| Plasma half life mean (days) | 21 | 5.9 | 5.1 | 2.8 | 2.4 |
| Fractional turn-over rate (% day) mean | 6.9 | 24.0 | 10.6 | 37.0 | 72.0 |
| Fraction for each class in plasma* mean | 0.52 | 0.55 | 0.74 | 0.75 | 0.51 |

*This fraction represents the portion of the total immunoglobulins of each class that is found in the plasma.

Host responses are initiated only after bacteria or viruses have already colonized tissues or implants and are beginning to enhance their own defenses (antigen masking, replication, biofilm, toxins). The host defense strategies require time to reach peak responses. During this time period, serious infection may be established, especially in immunocompromised patients. The presence of tissue damage and foreign bodies lower thresholds of infection and diminishes effective responses.

In the last decade, intravenous immunoglobulins (IVIG) have become a major treatment regime for bacterial and viral infections and of primary and secondary immunodeficiency states. For example, Buckley et al., New Eng. J. Med. 325:110–117 (1991), describe using intravenous immune globulin in the treatment of immunodeficiency diseases, and Cometta et al., New Eng. J. Med. 327:234–239 (1992), describe the prophylactic intravenous administration of standard immune globulin and core-lipopolysaccharide immune globulin in patients at high risk of post-surgical infection. IVIGs are prepared from the pooled plasmas of large numbers of donors, and tend to have a broad representation of antibodies. Specifically, pooled polyvalent human globulins usually contain antibodies for ubiquitous pathogens such as H. influenza type b, pneumococci, staphylococci, diphtheria, tetanus, respiratory synctial virus (RSV), measles, cytomegalovirus (CMV), and varicella zoster virus. Antibody concentrations from lot to lot and from manufacturer to manufacturer usually vary only two to four fold when measured by antibody binding assays. However, functional assays often show much larger lot to lot variations as do antibody concentrations to less common pathogens (see, Siber et al., "Use of immune globulins in the prevention and treatment of infections", Current Clinical Topics in Infectious Disease, Remington J S, Swartz M M, eds., Blackwell Scientific, Boston, 12:208–257 (1992)).

IVIG therapy has been reported to be beneficial for more than thirty five diseases produced by immunopathologic mechanisms. Passive immunization against infections has been particularly successful with immune globulins specific for tetanus, hepatitis B, rabies, chickenpox, and cytomegalovirus. Passive immunization depends on the presence of high and consistent titers of antibodies to the respective pathogens in each preparation.

Nosocomial infections are derived from the hospital or clinical setting, and are also a serious problem. Specifically, bacteria and viruses present in the hospital or clinic can infect a recovering patient and put the patient at risk or prolong the recovery period. A patient's risk factors for nosocomial infection can be intrinsic, such as susceptibility to infection due to immunosuppression, or extrinsic, such as invasive medical interventions (e.g., surgery or use of medical devices such as catheters, ventilators, etc.). Staphylococcus aureus is an important cause of nosocomial infection, especially nosocomial pneumonia, surgical wound infection, and bloodstream infection (Panlilio et al., Infect. Cont. Hosp. Epidemiol. 13:582–586 (1992)). Other pathogens commonly associated with nosocomial infection include, but are not limited to, Escherichia coli, Pseudomonas aeruginosa, Enterococcus spp., Enterobacter spp., coagulase-negative staphylococci (CNS), and Candida aibicans (Emori et al., Am. J. Med. 91: (suppl 3B) 289S–293S (1991)). Hospitals and clinics typically employ strict sterilization procedures and use antibiotics such as methicillin, oxacillin, and nafcillin to combat virulent bacterial pathogens. However, nosocomial infections still occur in great numbers and are expected to increase with an aging population.

The use of intravenous immunoglobulins to prevent nosocomial infections has been discussed in Siber, New Eng. J. Med. 327:269–271 (1992). Passive immunization against infections has been particularly successful using immune globulins containing antibodies specific for tetanus, hepatitis B, rabies, chickenpox, and CMV. However, it is reported that there is an inconsistent benefit from using intravenous immune globulins to prevent nosocomial infections. This may be due to variable lot-to-lot levels of antibodies to the more common nosocomial pathogens and emerging new serotypes.

U.S. Pat. No. 4,412,990 to Lundblad et al. discloses an intravenous pharmaceutical composition containing immunoglobulin (IgG) and fibronectin that exhibits a synergistic opsonic activity which results in enhanced phagocytosis of bacteria, immune complexes, and viruses.

U.S. Pat. No. 4,994,269 to Collins et al. discloses the topical use of monoclonal antibodies for the prevention and treatment of experimental P. aeruginosa lung infections. Specifically, the antibodies are administered via aerosol spray to the lungs. Results show beneficial effects in the treatment of Pseudomonas pneumonia.

U.S. Pat. No. 4,714,612 to Nakamura et al. discloses the use of a non-specific gamma globulin IgG in a mouthwash for preventing gingivitis. Ma et al., Arch. Oral Biol., 35 suppl:115S–122S, 1990, discloses the use of monoclonal antibodies specific for Streptococcus mutans in a mouthwash. Experiments showed control subjects experienced recolonization with Streptococcus mutans within two days, but those treated with the monoclonal antibodies remained free of Streptococcus mutans for up to two years.

SUMMARY OF THE INVENTION

It is an object of this invention to provide a new method for the direct, concentrated local delivery of passive immunity.

It is another object of this invention to provide new compositions which include a full repertoire of immunoglobulin classes (IgG, IgA, IgM), and new methods for prophylactic positioning of the compositions wherein the compositions are applied directly to wounds, burns, tissues, and biomaterial devices as a creme, ointment, coating, layer, or the like, to prevent and treat infection from microorganisms and viruses.

It is another object of this invention to provide new compositions, which can include a full repertoire of immunoglobulin classes (IgG, IgA, IgM), and has a broad spectrum of antibodies with elevated antibody titers to specific microorganisms that commonly cause biomaterial, burn, mucosal, tissue, surgical wound, and body cavity infections.

It is another object of this invention to provide a biocompatible layer with an immunoglobulin composition containing a broad spectrum of antibodies to specific infectious pathogens immobilized thereon that is placed in-situ in the treatment of wounds and burns.

It is another object of this invention to coat catheters and the like, which are used for acute or chronic treatment, with a composition containing a broad spectrum of immunoglobulins which includes antibodies to prevent the types of infections which often result with the long term use of these devices.

It is another object of this invention to provide a method of using immunoglobulin compositions of broad spectrum and high concentration, whereby bacteria are pre-opsonized in-situ for enhanced phagocytosis and killing.

According to the invention, the direct, concentrated local delivery of passive immunity is accomplished by applying a composition having a full repertoire of immunoglobulins (IgG, IgM and IgA) to biomaterials, implants, tissues, and wound and burn sites. The composition preferably has elevated concentrations of certain immunoglobulin classes (IgG, IgM, and IgA), and elevated antibody titers to specific microorganisms that commonly cause biomaterial, burn, mucosal, tissue, surgical wound, and body cavity infections. Compositions within the practice of this invention may take several forms, including cremes, gels, ointments, lavage fluids, sprays, lozenges, coatings, layers, or any other topical mode of administration. In addition, the compositions may be combined with or immobilized on a biocompatible or biodegradable material, or be impregnated in a matrix material for sustained release. The compositions can be used for both prevention and treatment of infections.

In oral applications, the composition would ideally be provided as a lozenge, mouthwash, or spray, while in trauma patients the composition may be best applied as a creme or ointment, or as part of a biomaterial implant or fixation device. The immunoglobulins and other antibodies of the present compositions can be immobilized on a biocompatible material which is placed in-situ in a patient's wound or burn site, or be coated on a catheter or the like that is inserted in a body cavity.

Application of the compositions should occur within six hours or at a time of trauma or of cleaning the wound or burn site so that bacteria present therein or arriving at the site will be pre-opsonized for phagocytosis and killing prior to their replication and potential toxin production. Furthermore, application prior to biofilm formation reduces the adhesion of infectious bacteria to biomaterial implants and certain tissues, and helps prevent the formation of a biofilm which would block contact of the infectious bacteria with circulating immunoglobulins and macrophages.

In summary, tissue, wound or biomaterial surface pretreatment at the time of surgery or shortly after trauma, would allow the effective use of a full repertoire of immunoglobulins, including IgG, IgM, and IgA at high concentrations without side effects, before colonization and infection develops.

DETAILED DESCRIPTION OF THE PREFERRED EMBODIMENTS OF THE INVENTION

It is well established that the microorganisms that are causative agents of biomaterial-related infections have a strong affinity for binding to the surfaces of biomaterials (See, Gristina et al., "Materials, Microbes and Man: The Problem of Infection Associated with Implantable Devices", Current Perspectives on Implantable Devices, Vol. 1, pp. 71–137 (1989), JAI Press, Inc.). This affinity allows these causative agents of serious biomaterial related infections to colonize the surfaces of biomaterials. At the moment of implantation, a polymeric biomaterial, such as a vascular graft or the like, is a ready site for competitive bacterial or tissue colonization. In vivo, available bacteria may defeat the host tissue cells in a race for the polymer's surface and thus cause infection, resulting in the failure of tissue integration, of the polymer (Gristina et al., Zbl. Bakt. Suppl. 16, Gustav Fischer Verlag, Stuttgart, New York, pp. 143–157 (1987)). Bacteria colonized on the surface of a biomaterial become protected from antibiotics and host defenses (immunoglobulins) by a biofilm and continuously maintain the infection in the patient, despite antibiotic medication. The biofilm also provides the bacteria with some protection from phagocytes, a major mechanism of host defense. Experience has shown that phagocytes have great difficulty in their attempts to phagocytose and kill the offending organisms growing at the biomaterial-host tissue interface, particularly when bacteria are embedded in a biofilm.

Experiments have shown that hyperimmune sera made in rabbits by injecting rabbits with killed Staphylococcus epidermidis (RP12 strain) and/or the polysaccharide capsular slime extracted from S. epidermidis strain RP12 markedly reduces the adherence of the RP12 strain to the surface of the biomaterial polymethylmethacrylate (PMMA). S. epidermidis, which is usually thought of as a nonpathogenic commensal human skin saprophyte, has emerged as a serious pathogen in biomaterial-related infections as well as in immunocompromised patients (Gristina et al., Zbl. Bakt. Suppl. 16, Gustav Fischer Verlag, Stuttgart, New York, pp. 143–157 (1987)). In these experiments, standard suspensions of the RP12 strain of S. epidermidis were incubated for thirty minutes with 1:200 dilutions of either normal rabbit serum or hyperimmune serum against the RP12 strain of S. epidermidis. This allowed the specific antibodies to bind to the surface polysaccharide molecules of the organisms. These suspensions were washed with phosphate buffered saline (PBS) and standard samples of PMMA were added to the various preparations. The bacteria-PMMA preparations were incubated for sixty minutes, and the PMMA samples were then washed three times with PBS to remove loosely attached bacteria. The PMMA samples were sonicated for ten minutes in PBS and the supernatants were diluted and plated on Trypticase-Soy agar to determine the number of colony forming units (CFU) that adhered to the PMMA samples. Table 3 presents the experimental results.

TABLE 3

| | | |
|---|---|---|
| Effect of Anti-RP12 Antisera on the Binding of the RP12 Strain of S. epidermidis to PMMA | | |
| PMMA plus RP12 incubated with | CFU Bound to PMMA | Percent inhibition |
| PBS | 393,000 | |
| Normal Serum (1:200) | 319,000 | |
| Antiserum (1:200; lot 11949) | 105,000 | 67[a] 73[b] |

[a]Calculated as the percent inhibition of anti-sera treated RP12 versus RP12 pretreated with normal sera.
[b]Calculated as the percent inhibition of anti-sera-treated RP12 versus RP12 pretreated with only PBS.

Table 3 shows that normal serum has some inhibitory effects. This is not surprising because a low level of antibody would be expected in the sera of rabbits and humans because *S. epidermidis* is a normal flora microorganism of the skin.

The immunoglobulin G (IgG) fraction was isolated from the antiserum (11949) and tested for its capacity to block adherence of the RP12 strain. Gristina, *Science* 237:1588–1595 (1987), points out that inhibiting bacterial adhesion is an important parameter in reducing biomaterial-centered infection. Polymethylmethacrylate (PMMA) samples incubated with RP12 suspended in PBS (no antibodies) bound 604,000 CFU per sample. In sharp contrast, PMMA samples incubated with RP12 preincubated with the hypermimmune IgG only bound 33,000 organisms. This represents a 94 percent inhibition of binding of RP12 to PMMA.

Kojima et al., *J. Infectious Dis.* 162:435–441 (1990), disclose similar experiments where antibody to the capsular polysacharide/adhesin (PS/A) protects rabbits against catheter related bacteremia due to coagulase negative staphylococci. In vitro experiments with antibody raised to PS/A inhibited adherence of homologous and heterologous adhesin-positive coagulase negative staphylococci to silicon elastomer catheter tubing in a dose-response fashion.

For comparison purposes, experiments were conducted to determine the capacity of antiserum (11949) to inhibit the binding of various strains of coagulase negative staphylococci. Six strains of coagulase negative staphylococci were incubated with the anti-RP12 antiserum (11949) to determine whether specificity exists with respect to blocking the adherence of the different strains to PMMA. The inhibition assay described above was performed for each strain and the results are set forth in Table 4.

TABLE 4

Capacity of Anti-RP12 Antiserum to Block Adherence of Six Strains of Coagulase Negative Staphylococci to PMMA

| Strain | CFU/Sample | % Inhibition |
|---|---|---|
| RP12 | 198,000–6,000 | 67–99 |
| SP2 | 162,000 | 73 |
| SE360 | 602,000 | 0 |
| LD1 | 126,000 | 79 |
| ERI | 610,000 | 0 |
| RP62A | 695,000 | 0 |

The results in Table 4 indicate that there is specificity in inhibition and that serologic groups of adhesins exist.

From the above data in Tables 3 and 4, this invention contemplates that hyperimmune sera raised against a pool of adhesins is needed to block adherence of various coagulase negative serotypes of staphylococci and other bacteria and viruses to biomaterials and to lower the risk of infection at surgery.

IVIG compositions are commercially available (e.g., GAMMAGARD® available from Baxter Healthcare Corporation), and are used in the treatment of primary immunodeficiency states such as congenital agammaglobulinemias, common variable immunodeficiency, Wiskott-Aldrich syndrome, etc. In addition, IVIG compositions have been used to prevent bacterial infections in patients with hypogammaglobulinemia and/or recurrent bacterial infections associated with B-cell Chronic Lymphocytic Leukemia. Siber et al., "Use of immune globulins in the prevention and treatment of infections", Remington I. S. and Swartz M. N. eds., *Current Clinical Topics in Infectious Disease*, Vol. 12, Blackwell Scientific, pp. 203–257, 1992, provides a thorough review of the use of intravenous immunoglobulins.

The major benefit of the intravenous immunoglobulins may be to opsonize bacteria for phagocytosis and enhance clearance of bacteria or their products. Additional benefits may be the neutralization of endotoxins and exotoxins, down regulation of interleukin-1 (IL-1) and TNF responses, and the recruitment of neutrophils from storage pools via C3 and C5 fragments. However, intravenous immunoglobulins can have detrimental effects, including the generation of immune complexes between exogenous antibody and large amounts of microbial antigens with the ensuing release of inflammatory mediators, blockade of Fc receptors or of C3 fixation leading to impaired clearance mechanisms, enhanced release of toxic products such as endotoxin or bacterial cell wall constituents due to complement mediated bacterial lysis. Experiments with rats have shown that high doses of intravenous immunoglobulins have enhanced mortality rates.

In addition, Siber et al., "Use of immune globulins in the prevention and treatment of infections", Remington I. S. and Swartz M. N. eds., *Current Clinical Topics in Infectious Disease*, Vol. 12, Blackwell Scientific, pp. 203–257, 1992, report that the administration of intravenous immunoglobulins did not reduce the incidence of bacteremias or mortality in trauma, major surgery, and burn victims.

This invention is particularly directed to new broad spectrum immunoglobulin compositions with a full repertoire of immunoglobulin classes (IgG, IgA, IgM) which are used to prevent and treat infections associated with major surgery, burns, trauma, and biomaterial devices and implants. In contrast to IVIG compositions, the compositions of the present invention are applied directly to the wound or burn site, or the biocompatible device or implant (including metal and polymeric materials).

It is probable that intravenous delivery routes cause serum dilution so that only low concentrations of antibodies reach the specific target site. The formation of biofilm protected infections, and limited diffusion, at traumatized tissue sites or in sites of poor vascularity (musculoskeletal and joints, burn sites) is also a likely cause for the ineffectiveness of IVIGs noted by Siber et al. against trauma. Major trauma also increases catabolic effects which may alter half-life of IVIG preparations. The use of IVIG in established infection after microorganisms have adhered, produced toxins, or are intracellular, is also less likely to be effective. IVIG prophylaxis has been believed not to prevent acquisition of the pathogen (see, Mandell et al., Eds., *Principles and Practice of Infectious Disease*, 2nd ed., John Wiley & Sons, New York, 1985, pp. 37–43). This is a misconception because IVIG is usually given after infection is established. The applicants also note that even if IVIG were given before infection, effective levels of immunoglobulins would not be available to intercept pathogens at entry sites or portals such as on biomaterials, on burned or damaged tissues, and on mucosal surfaces, before or shortly after contamination because of dilution and deficient circulation.

The inconsistent benefit of immune globulin in preventing nosocomial and post traumatic and burn infections may, in part, be explained by the variable levels of antibodies in standard preparations, as well as the required absence of IgA and IgM from IVIG preparations to prevent side effects. In 1992, a *New England Journal of Medicine* report stated, "Little is known about the variability in levels of antibodies to more common nosocomial pathogens, such as coagulase-negative staphyloccoci, or about the nature of the antibodies that confer protection, or even whether antibodies have a role in preventing infections associated with indwelling devices" (see, Siber, *New Eng. J. Med.*, 327(4):269–271 (1992)).

This invention solves the short-comings of IVIGs in preventing and treating infections secondary to trauma, burns, surgery, and biomaterials by applying a full repertoire immunoglobulin composition to tissue surfaces and biomaterials to prevent microbial adhesion and colonization (the acquisition of pathogens) and to pre-opsonize microbes in-situ for enhanced phagocytosis and killing. By preventing adhesion to surfaces and by opsonizing bacteria on arrival and shortly afterward, bacteria are identified, made vulnerable, and targeted for neutrophil and macrophage phagocytosis and killing while bacterial numbers are low before they can reproduce, release toxins, destroy tissue and form protective biofilms. This process also assists antibiotic strategies, since bacteria are more vulnerable before attachment to surfaces.

The use of applied coating concentrates of globulins to tissue, mucosal and biomaterial surfaces allows high dosages of IgA and IgM, in addition to IgG, to be delivered directly to a wound. Currently available IVIG preparations have IgA and IgM selectively removed to prevent anaphylactoid reactions. Anaphylactoid reactions are not a danger when an immune globulin composition is used locally at a wound or burn site. Including IgA in a creme, ointment, or lavage fluid that will be applied to a wound or biomaterial is advantageous since IgA is known to block adhesion of bacteria and to neutralize viruses. IgM enriched IVIG preparations have been reported to be highly effective against gram negative bacteria and endotoxins (see, Behre et al., *Antimicrobial Agents and Chemotherapy*, October 1992, pp.2139–2146); therefore, including elevated concentrations of IgM in a creme, ointment or lavage fluid is preferred. Macrophages and complement are naturally mobilized and concentrated at wound sites and are available to respond to the bacteria opsonized by the therapeutically delivered polyvalent globulins of the inventive compositions. The generation of immune complexes and inflammatory mediators, as occurs with high doses of IV preparations, is diminished or prevented by local delivery. Equine or other animal derived plasma products, if utilized for human or animal therapy, are also less likely to cause side effects by this method.

In summary, wound or biomaterial surface pretreatment, at time of surgery or shortly after trauma, allows the effective use of a full repertoire of globulins including IgG, IgM, and IgA at high concentrations without side effects, before infection starts.

The immunoglobulin preparations of the present invention can be prepared by a number of methods. It is contemplated that an ideal method for obtaining the immunoglobulin preparations is to first obtain the immunoglobulin fraction (cold ethanol fractionation process) from the sera from a large number of human donors. As needed, the immunoglobulin pool will be fortified with hyperimmune immunoglobulins obtained from immunized donors or donors with high antibody titers for specified bacteria or viruses. In addition, monclonal antibodies for specified bacteria and viruses can be added to the compositions.

In this invention, the full repertoire of immunoglobulin classes, IgG, IgA, IgM, is preferably used in the ointments, cremes, lavage fluids, etc.; however, the ointments, cremes, and lavage fluids could contain only IgG if desired. Preferably, the immunoglobulins will be concentrated for high dosages. The immunoglobulins will constitute 0.1–20 percent by weight of the ointment, creme, lavage fluid, etc., with higher concentrations preferred (e.g., 10–20 percent by weight). If monoclonal antibodies specific for certain microrganisms are added to the immunoglobulin compositions, they will typically be present at 0.01–1 percent by weight. The ointments, cremes, or lavage fluids will be used locally by direct application to a wound or burn, or as a wash or coating for a biomaterial device or implant (e.g., Catheter). In addition, the compositions can be impregnated in or immobilized on a matrix carrier (e.g., fibrin, collagen, etc.) for sustained release or elution therefrom. The matrix carrier can be in the form of a wound dressing or other material placed in-situ at a wound or can be coated on the body contacting surfaces of a biomaterial implant or device (catheter, etc.). The immunoglobulin compositions will ordinarily be provided to patients at 2–100 mg/kg body weight; however, variation from this dose range can occur. The size of the wound or biomaterial implant can dictate that smaller or larger quantities of the compositions be used.

Table 5 lists the concentration ranges and mean values for immunoglobulins found in normal sera, as well as the proposed concentrations of immunoglobulins to be used in wash lavage or wash fluid preparations contemplated by this invention.

TABLE 5

Range of concentrations of immunoglobulins in normal human sera in mg/dl as compared to the concentrations used in lavage fluid preparations of the present invention

| Immunoglobulin | Normal Serum Level | Mean | Lavage |
| --- | --- | --- | --- |
| IgG | 600–1600 | 989 | 500–2000 |
| IgM | 45–150 | 100 | 100–300 |
| IgA | 60–330 | 200 | 100–500 |

As discussed above, compositions with elevated levels of IgM and IgA (200–300 mg/dl and 400–500 mg/dl, respectively) would provide benefits in blocking adhesion of bacteria to biomaterials and certain tissues, which will prevent microbial pathogen adherence and colonization as well as have enhanced activity towards gram negative bacteria and endotoxins. In addition, concentrated levels of IgA provide enhanced neutralization of viruses and prevent viruses from infecting cells lining the mucocutanous surfaces of the body. Since the broad spectrum immunoglobulin compositions are being locally delivered, anaphylactoid reactions are avoided. Furthermore, side effects associated with IVIG (IgG only) preparations such as increased pulse rate and blood pressure are avoided by local delivery, thereby allowing elevated concentrations of IgG (1700–2000 mg/dl or higher) to be administered to a patient. Concentrated levels of immunoglobulins (IgG, IgM, and IgA) enhance the in-situ pre-opsonization strategy contemplated by this invention. The lavage fluids of the present invention will ordinarily be diluted in saline at neutral pH and will include stabilizing agents such as glucose (up to 20 mg/ml), polyethylene glycol (up to 2 mg/ml), glycine (up to 0.3M), and albumin (preferably human up to 3 mg/ml). Buffer agents (e.g., acetate) could be included in the lavage fluids. Other base fluids (ethanol, etc.) and stabilizing agents (maltose, etc.), and the like may also be used for the lavage fluids of the present invention. The lavage fluids of the present invention could be used as wash for all routine surgeries including fiberoptic procedures, will have vaginal and genitourinary applications, and can be used as a peritoneal wash or combined with continuous peritoneal dialysate solutions.

Table 6 lists the concentration ranges of immunoglobulins in cremes, syrups, or other special viscous carriers (including lozenges and suppositories), contemplated by this invention.

TABLE 6

Range of concentrations of immunoglobulins in mg/dl in a viscous carrier (creme, ointment, syrup) of the present invention.

| Immunoglobulin Class | Composition Level |
| --- | --- |
| IgG | 2,500–20,000 mg/dl |
| IgM | 500–3,000 mg/dl |
| IgA | 500–5,000 mg/dl |

Cremes, ointments, gels, syrups, and the like, which are applied to the surfaces of biomaterial devices and implants (catheters, etc.), or to the surfaces of skin and of bandages and other dressings, as well as burned or damaged tissue provide an ideal mechanism for maintaining immunoglobulins in-situ for extended periods of time. Because the carrier is a lotion, syrup, oil, or thickening agent, the immunoglobulins can be concentrated to levels 5–10 times greater than that used for lavage or wash fluids. As discussed above, stabilizers and other agents will be combined with the creme, ointment, syrup, cough drops, etc. Sprays, syrups, and cough drops containing the full repertoire immunoglobulin compositions are an ideal method for respiratory infection prevention and for delivery in times of epidemic risk.

The immunoglobulin preparations to be used in this invention will be tested for opsonic activity, viral neutralizing activity, and bactericidal activity with the addition of the complement system in vitro to evaluate and standardize the potency of the preparations. When activities are suboptimal, the preparations will be either fortified with hyperimmune globulins or monoclonal antibodies to provide the necessary antibody spectrum and level to cover the microbial strain specificities required for effective prophylaxis and/or treatment. Table 7 lists the major candidates for prophylaxis and treatment of wound, burn, nosocomial, and oral and respiratory infections of all types (including implanted devices).

TABLE 7

| Microorganism | Specific Antibodies Estimated Effective Concentration |
|---|---|
| *Staphylococcus aureus* | 1–50 μg/ml |
| *S. epidermidis* | 1–50 μg/ml |
| Coagulase Neg. Staph. | 1–50 μg/ml |
| Streptococcus (Groups A,B,and D) | 1–50 μg/ml |
| *Pseudomonas aeruginosa* | 1–50 μg/ml |
| *Escherichia coli* | 1–50 μg/ml |
| Enterobacter spp. | 1–50 μg/ml |
| *Klebsiella pneumoniae* | 1–50 μg/ml |
| *Streptococcus pneumoniae* | 1–50 μg/ml |
| *S. mutans* | 1–50 μg/ml |
| *Hemophilus influenzae* | 1–50 μg/ml |
| Proteus spp. | 1–50 μg/ml |
| *Bacteroides gingivalis* | 1–50 μg/ml |
| *Streptococcus pyogenes (Group A)* | 1–50 μg/ml |
| *Mycoplasma pneumoniae* | 1–50 μg/ml |
| Respiratory Syncytial Virus | 1–50 μg/ml |
| Influenza Virus (A, B, and C) | 1–50 μg/ml |
| Rhinovirus | 1–50 μg/ml |

An immunoglobulin composition of this invention which could be used universally in the treatment and prophylaxis of wounds, burns, nosocomial infections, and oral and respiratory infections would have specific antibodies against each of the groups of potential pathogens of Table 7 within the above concentration ranges. In particular applications, the antibody titers for specific pathogens in the immunoglobulin compositions can be five to twenty times greater than those specified in Table 7 (e.g., 5–1000 μg/ml)- Compositions containing lower or higher antibody titers to less or more than the above listed pathogens might also provide protection from infections. For instance, a preparation containing high titer levels for *S. aureus* and *P. auruginosa* may provide acceptable results. However, it should be understood that wound, burn, and nosocomial infections, etc., are commonly polymicrobial and the result of a wide variety of pathogens, therefore, hyperimmune immunoglobulin compositions should contain high titers of antibodies for at least two and preferably three, four, or five, or more, of the pathogens listed in Table 7. Note that Table 4 above demonstrates that hyperimmune immunoglobulin compositions raised against a pool of infectious pathogens provides the optimum protection. Therefore, this invention contemplates a "polyclonal cocktail" of antibodies specific for key pathogens that normally gain entrance to all wounds, etc., as needed and determined by in vitro functional assays.

The invention also contemplates the use of monoclonal cocktails prepared against specific epitopes on the immunogenic antigens from the pathogens in Table 7. In this case, the effective concentrations would be 1–2 orders of magnitude lower than those indicated in Table 7. Specifically, concentrations of 0.01–5 μg/ml of monoclonal antibodies would be present in the compositions.

Furthermore, the invention also contemplates supplementing immunoglobulin compositions with monoclonal antibodies specific for the relevant pathogens as needed. As discussed above, the concentration of the monoclonal antibodies added to the compositions would be in the 0.01–5 μg/ml range.

Immunoglobulin polyclonal cocktail preparations, monoclonal cocktails, and immunoglobulin preparations supplemented with monoclonal antibodies, can be prepared for specific applications to combat the major pathogens associated with those applications. The immunoglobulins for specific pathogens would preferably have an effective concentration of 1–50μg/ml of antibodies for those pathogens, and could have higher effective concentrations (e.g., 5–1000 μg/ml) as described above. In addition, if the compositions contained monoclonal antibodies specific for the pathogens associated with a particular application, they would be present at a concentration of 0.01–5 μg/ml. The compositions will contain those antibodies which are against the most clinically relevant strains or types of organisms.

The major pathogens to defend against will vary depending on the site of infection. For example, a contact lens wash solution should include immunoglobulins with antibodies or monoclonal antibodies specific for *S. epidermidis* and *P. aeruginosa*. In genitourinary catheter applications, the compositions should include immunoglobulins with antibodies or monoclonal antibodies specific for at least two of the following microorganisms: *E. coli, Enterobacter spp., Proteus spp.,* and *P. aeruginosa*. In intravenous, intraarterial, or intraperitoneal catheter applications, the compositions should include immunoglobulins with antibodies or monoclonal antibodies specific for at least two of the following microorganisms: *S. aureus, P. aeruginosa, E. coli,* and *S. epidermidis*. Compositions to be used with wound (surgical or otherwise) and burn dressings should include immunoglobulins with antibodies or monoclonal antibodies specific for at least two of the following microorganisms: *S. aureus, Enterobacter spp., S. epidermidis,* and *P. aeruginosa*. Compositions to be used in combination with biomaterial implants and devices (catheters, artificial hearts, etc.), should include immunoglobulins with antibodies or monoclonal antibodies specific for at least two of the following pathogens: *S. epidermidis, S. aureus, E. coli, Enterobacter spp.,* or *P. aeruginosa*. Oral compositions (lozenges, syrups, etc.) should include immunoglobulins with antibodies or monoclonal antibodies specific for at least two of the following pathogens: *S. aureus, S. mutans,* and *Bacteroides gingivalis*. Compositions used for oral, nasopharyngeal, and respiratory infections (e.g., aerosol and non-aerosol sprays, lozenges, syrups, etc.) should include immunoglobulins with antibodies or monoclonal antibodies specific for at least two of the following pathogens: *Streptococcus mutans, B. gingivalis, S. pyogenes* (group A), *S. pneumoniae, K. pneumoniae, P. aeruginosa, S. aureus, M. pneumoniae, H. influenzae,* Respiratory Syncytial Virus, Influenza Virus (A, B, and C), and rhinoviruses.

The time of application of the full repertoire immunoglobulin compositions is important. Within six hours after a surgical wound or burn site occurence, or after cleaning a wound or burn, a biofilm is formed over the site which includes bacteria and viral agents. The biofilm can shield the microbial agents against antibiotics, intravenous immunoglobulins, and phagocytes; therefore, the biofilm acts a repository for pathogens which cause chronic and recurrent infections. By applying the full repertoire broad spectrum immunoglobulin composition at the wound or burn site immediately after cleaning or surgery and prior to bacterial attachment or biofilm formation prevents adhesion of the bacteria and pre-opsonizes the bacteria for phagocytic killing and removal before toxin release.

The protective activity of the full repertoire broad spectrum immunoglobulin composition could be enhanced by providing antibiotics, antivirals, antiinflammatory and healing compounds in combination with the immunoglobulins. For example, biocides, surfactants, bacterial blocking receptor analogues, cytokines, growth factors, macrophage chemotactic agents, cyphalosporins, aminoglycosides, fluoroquinolones, etc., could be provided at therapeutically acceptable levels in the lavage fluids, sprays (both aerosol and non-aerosol), ointments, Cremes, syrups, lozenges, suppositories, and the like, of the present invention.

The full repertoire broad spectrum immunoglobulin compositions may ideally be immobilized within fibrin, collagen, gelatin, hyaluronan (hyaluronic acid), polysacharide, or other biocompatible or biodegradable materials that are to be placed in-situ at a wound or burn site. This would insure that antibodies to particular pathogens remain present throughout the healing process. The antibodies of the immunoglobulin compositions could ideally have a slow, sustained release or elution from the matrix materials. Ideally, the layers of the matrix materials with immobilized immunoglobulins would be biodegradable. Antibiotic, antiviral, antiinflammatory and healing compounds would ideally be used in combination with the immunoglobulin composition, and these compounds would be impregnated into the biocompatible material. Catheters, ventilators, and implantable devices such as vascular grafts and total joints would ideally have the full repertoire broad spectrum immunoglobulin compositions of the present invention, as well as antibiotic and antiviral compounds, immobilized on an external or internal, body or blood contacting surface. Implantable devices are frequently responsible for severe infections; therefore, the compositions of this invention would have immediate application in combination with these devices.

It should be understood that the hyperimmune globulin compositions of the present invention have veterinary applications as well as human health care utility.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A method for preventing infections in human and animal hosts that are derived from implanted biomaterials, comprising the steps of:

coating a biomaterial to be implanted in a human or animal host with an antimicrobial composition containing 0.1–20% by weight of a mixture of antibodies within a pharmaceutically acceptable carrier wherein said mixture of antibodies is selected from the group consisting of IgG, IgG in combination with IgM and IgA, IgG in combination with monoclonal antibodies, IgG in combination with IgM and IgA and monoclonal antibodies, and monoclonal antibodies;

implanting said biomaterial in said human or animal host at a biomaterial implant site, said antimicrobial composition coated on said biomaterial producing an immunocompetent inflammatory zone sufficient to prevent adhesion of microorganisms to said biomaterial and to pre-opsonize said microorganisms for rapid intracellular killing by host defense mechanisms, said step of coating being performed prior to said step of implanting or within a period of six hours after implanting; and preventing or reducing infections in said human or animal host at said biomaterial implant site with said antimicrobial composition.

2. The method of claim 1 further comprising the step of selecting said biomaterial to be a catheter.

3. The method of claim 1 further comprising the step of selecting said biomaterial to be a joint.

4. The method of claim 1 further comprising the step of selecting said biomaterial to be an articial heart.

5. The method of claim 1 further comprising the step of selecting said biomaterial to be a vascular graft.

6. The method of claim 1 further comprising the step of selecting said biomaterial to be a ventilator.

7. A method for preventing infections in human and animal hosts that are derived from implanted biomaterials, comprising the steps of:

coating a biomaterial to be implanted in a human or animal host with an antimicrobial composition containing IgG at a concentration ranging from 500–20,000 mg/dl;

implanting said biomaterial in said human or animal host at a biomaterial implant site, said antimicrobial composition coated on said biomaterial producing an immunocompetent inflammatory zone sufficient to prevent adhesion of microorganisms to said biomaterial and to pre-opsonize said microorganisms for rapid intracellular killing by host defense mechanisms, said step of coating being performed prior to said step of implanting or within a period of six hours after implanting; and preventing or reducing infections in said human or animal host at said biomaterial implant site with said antimicrobial composition.

8. The method of claim 7 further comprising the step of selecting said biomaterial to be a catheter.

9. The method of claim 7 further comprising the step of selecting said biomaterial to be a joint.

10. The method of claim 7 further comprising the step of selecting said biomaterial to be an articial heart.

11. The method of claim 7 further comprising the step of selecting said biomaterial to be a ventilator.

12. The method of claim 7 further comprising the step of selecting said biomaterial to be a vascular graft.

* * * * *